United States Patent [19]
Sabolich et al.

[11] Patent Number: 6,077,300
[45] Date of Patent: *Jun. 20, 2000

[54] ARTIFICIAL LIMB WITH ANATOMICALLY CONFIGURED SOCKET

[75] Inventors: John A. Sabolich; Kevin M. Carroll, both of Oklahoma City, Okla.

[73] Assignee: NovaCare Orthotics & Prosthetics East, Inc., King of Prussia, Pa.

[*] Notice: Under 35 U.S.C. 154(b), the term of this patent shall be extended for 118 days.

[21] Appl. No.: 08/636,421

[22] Filed: Apr. 23, 1996

[51] Int. Cl.⁷ ..................................................... A61F 2/80
[52] U.S. Cl. ................................................ 623/37; 623/33
[58] Field of Search ................................. 623/36, 37, 33

[56] References Cited

U.S. PATENT DOCUMENTS

| | | |
|---|---|---|
| 2,634,424 | 4/1953 | O'Gorman . |
| 3,393,407 | 7/1968 | Kandel . |
| 3,671,980 | 6/1972 | Baird . |
| 3,889,301 | 6/1975 | Bonner, Sr. . |
| 4,307,056 | 12/1981 | Meyer ..................................... 264/222 |
| 4,432,101 | 2/1984 | Johnson . |
| 4,655,779 | 4/1987 | Janowiak ................................. 623/37 |
| 4,842,608 | 6/1989 | Marx et al. ............................... 623/33 |
| 4,872,879 | 10/1989 | Shamp ..................................... 623/36 |
| 4,911,724 | 3/1990 | Fikes ........................................ 623/37 |
| 4,921,502 | 5/1990 | Shamp ..................................... 623/33 |
| 4,923,475 | 5/1990 | Gosthnian et al. ........................ 623/37 |
| 4,988,360 | 1/1991 | Shamp ..................................... 623/33 |
| 5,108,456 | 4/1992 | Coonan, III ............................... 623/37 |
| 5,246,464 | 9/1993 | Sabolich ................................... 623/33 |
| 5,387,245 | 2/1995 | Fay et al. ................................. 623/37 |
| 5,405,405 | 4/1995 | Love ........................................ 623/37 |
| 5,507,836 | 4/1996 | Pohlig ...................................... 623/37 |

FOREIGN PATENT DOCUMENTS

| | | | |
|---|---|---|---|
| 2420335 | 10/1979 | France ..................................... 623/37 |
| 425629 | 2/1975 | U.S.S.R. .................................. 623/37 |
| 92/08175 | 5/1992 | WIPO . |

OTHER PUBLICATIONS

K. Carroll & J. Sabolich, AK Socket Design, Bio–Mechanics, Feb. 1996, at 183.

K. Carroll & J. Sabolich, Transtibial Prosthetic Principals, Bio–Mechanics, Mar. 1996, at 29.

J. Sabolich, Contoured Adducted Trochanteric–Controlled Alignment Method (CAT–CAM); Introduction and Basic Principles, Orthotics and Prosthetics, vol. 9 No. 4, 1985, at 15.

*Primary Examiner*—David H. Willse
*Attorney, Agent, or Firm*—McKinney & Stringer, P.C.

[57] ABSTRACT

An improved above-the-knee prosthesis with an anatomically configured socket is characterized by one or more contours which correspond to a pre-selected anatomical contour of the upper or lower residual thigh. By exaggerating the depth of the contour in the socket as compared with the corresponding contour in the thigh, the socket grips the residual thigh and maintains the femur in proper alignment. The new channels and contours allow the patient using the socket to have improved rotational support and control over the prosthesis by providing structures which the muscles of the upper and lower residual thigh can "grip." The socket snugly contains the thigh and maintains it, throughout the gait cycle, in a proper anatomical position. This fit increases the comfort of the prosthesis and minimizes gait abnormalities common with other artificial limbs. The increased support helps maintain the physical condition of the residual limb. The extended and new channels allow the muscles of the patient's residual thigh to flex and contract against and around the channels, thereby reducing muscle atrophy.

4 Claims, 5 Drawing Sheets

ARTIFICIAL LIMB WITH ANATOMICALLY CONFIGURED SOCKET

FIELD OF THE INVENTION

The present invention relates generally to artificial limbs and, more particularly, to artificial limbs having sockets.

SUMMARY OF THE INVENTION

The present invention comprises a prosthesis for the residual thigh of an above-the-knee amputee. The prosthesis comprises a limb assembly and a socket in the limb assembly. The socket is characterized by one or more of the following anatomical contours: an elongate anterior-medial triangular depression channel shaped to conform substantially to an elongate triangular depression generally defined laterally by the sartorius muscle, medial-proximally by the lateral and inferior aspect of the adductor longus muscle, medial-distally by the anterior aspect of the gracilis muscle, and proximally by the inguinal ligament; an elongate anterior triangular depression channel shaped to conform substantially to an elongate triangular depression generally defined laterally by the proximal aspect of the sartorius muscle and the distal-medial aspect of the rectus femoris muscle, medially by the proximal-lateral aspect of the adductor longus muscle, and proximally by the inguinal ligament, wherein the triangular depression distally extends to the lateral aspect of the vastus medialis muscle, and wherein the triangular depression extends across the sartorius muscle and between the vastus medialis muscle and the rectus femoris muscle; an elongate medial triangular depression channel shaped to conform substantially to an elongate channel on the medial thigh generally defined proximally by the inferior border of the ramus of the ischium, anteriorly by the posterior aspect of the gracilis muscle, and posteriorly by the adductor magnus muscle, the semimembranosus muscle, and the semitendinosus muscle, wherein the elongate medial longitudinal channel is shaped to conform substantially to a channel which extends substantially to the distal end of the muscles of the residual thigh; an elongate posterior-lateral longitudinal channel shaped to conform substantially to an elongate channel on the posterior-lateral thigh generally defined anteriorly by the vastus lateralis muscle and posteriorly by the biceps femoris muscle-lateral head, wherein the elongate posterior-lateral longitudinal channel is shaped to conform substantially to a channel which extends substantially to the distal end of the muscles of the residual thigh; a posterior longitudinal triangular channel shaped to conform substantially to an elongate channel on the posterior thigh generally defined by the groove at the semitendinosus muscle and the biceps femoris muscle; a mid-lateral-posterior longitudinal channel shaped to conform substantially to an elongate channel on the lateral thigh generally defined posteriorly by the iliotibial band, anteriorly by the vastus lateralis muscle, proximally by the proximal aspect of the tensor-faciae latae muscle and the proximal-lateral aspect of the rectus femoris muscle, wherein the elongate channel is shaped to conform substantially to a channel which extends substantially to the distal end of the muscles of the residual thigh; a lateral-anterior longitudinal channel shaped to conform substantially to an elongate channel on the lateral-anterior thigh generally defined laterally-posteriorly by the vastus lateralis muscle and lateral-anteriorly by the rectus femoris muscle.

BRIEF DESCRIPTION OF THE DRAWINGS

FIG. 6 is a plan view of the socket shown in FIG. 2B.

DETAILED DESCRIPTION OF THE PREFERRED EMBODIMENTS

In U.S. Pat. No. 5,246,464, there is described an above-the-knee prosthesis with an anatomically configured socket having a generally triangular shape in cross section, compared to conventional quadrilateral sockets, and having various contours corresponding to selected anatomical structures of the residual thigh. While this socket of U.S. Pat. No 5,246,464 represents an improvement over conventional sockets, there remains a need for sockets which provide improved rotational control, increased comfort and continuous conditioning of the muscles of the residual limb. The present invention provides an improved anatomically configured socket for an above-the-knee prosthesis which offers these and other advantages which will become apparent from the following description of the preferred embodiments.

Figure 1:
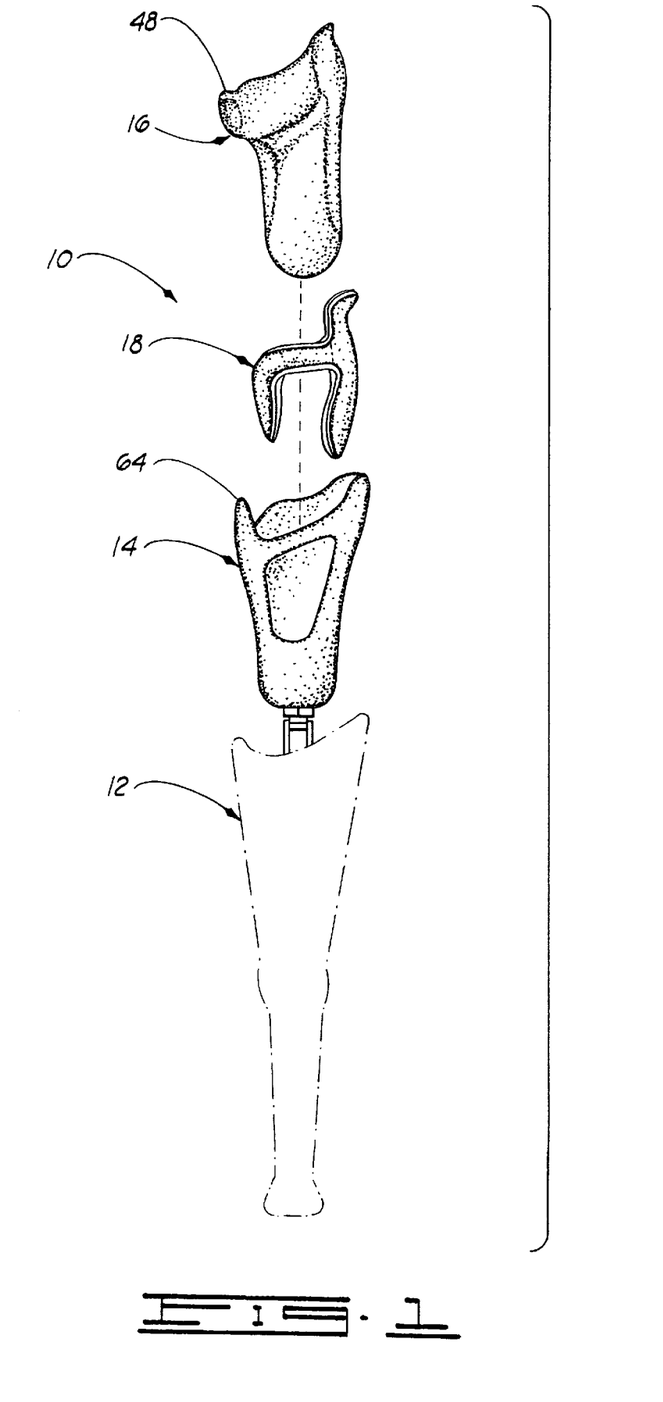
FIG. 1 is an exploded side elevational view of a prosthesis constructed in accordance with the present invention.

With reference now to the drawings in general and to FIG. 1 in particular, there is shown therein an elevational, exploded view of an above-the-knee prosthesis constructed in accordance with the present invention and designated generally by the reference numeral 10. The prosthesis 10 depicted in FIG. 1 comprises generally an external lower limb 12, an internal rigid frame 14 receivable in the limb 12, a socket 16 for securing the prosthesis to the residual thigh (not shown) and a system 18 of inflatable compartments. The techniques for producing, selecting and assembling of the other components of the prosthesis, such as the pylon, the foot, the knee joint and a cosmetic covering, are known to those of ordinary skill in the art and will not be described in detail herein. These components will be referred to herein collectively as "the limb."

As shown in FIG. 1, the socket 16 is formed separately and adapted to be supported within the frame 14. However, in some instances the socket may be formed integrally in the upper portion of the limb.

As indicated, the socket 16 is shaped to conform anatomically to the residual thigh on which it is to be worn. To this end, the socket 16 is provided with a plurality of contours which correspond to the anatomical contours of the residual limb. In most instances the socket 16 will be formed of a flexible and transparent material.

The procedure for fabricating the socket begins with a thorough interview and examination of the patient, with particular attention directed to the residual thigh. Adduction, abduction, flexion and extension are evaluated. The firmness of the tissue is observed. The presence and depth of various anatomical contours are noted and measurements are recorded. A suitable scale is utilized to note the relative depths of these contours.

Preferably, the depth of each anatomical depression or channel in the residual thigh is classified according to the following scale: Class I for ¼ inch; Class II for ½ inch; Class III for ¾ inch; Class IV for 1 inch; and Class V for 1¼ Similarly, the degree to which certain prominences protrude also are noted and classified as Class I, II, III, IV or V.

As used herein, the terms "depression" and "channel," when used in connection with the residual thigh, refer to areas which curve inwardly, that is, toward the inside of the thigh from the surface. Similarly, the terms "depression" and "channel," when used in connection with the socket or the model for the socket, refer to contours which curve toward the interior of the socket when viewed from the outside. Likewise, the terms "inverted channel" and "prominence" refer to contours which curve outwardly when viewed from the outside of the socket. Of course, it will be appreciated that a contour which forms a depression or channel when viewed from the outside of the socket will form a prominence or inverted channel when viewed from the inside of the socket and vice versa.

The examination of the patient proceeds by determining the midline of the body laterally by noting the position of the greater trochanter. The extent of abduction or adduction of the residual limb is noted, and whether the hips are level is observed. The ilio-femoral angle is measured.

The transverse ramus angle is measured next. This is the angle formed by the line of progression and the medial border of the ramus.

The shape of the ischial tuberosity is noted and classified as being alpha, beta or gamma.

The anterior-posterior dimension is measured from the adductor longus muscle to the ischial tuberosity. Care is taken to compress the lateral thigh with one hand while measuring medially with a ruler. This will ensure that the measurement is not distorted as a result of tissue compression.

The length of the residual limb is measured medially from the perineum using a rigid ruler, and this is transferred to the lateral side of the residual limb. The distance between the uppermost point of the ruler on the lateral side to the apex of the greater trochanter is taken.

Next, the skeletal medial-lateral dimension of the residual limb is measured from the ischial tuberosity to the apex of the greater trochanter. The medial-lateral dimension is taken from the ischial tuberosity parallel to the floor.

The soft tissue measurements are taken medio-laterally beginning immediately below the ischial tuberosity and ramus and then in two inch increments to the distal end of the residual limb. The angular circumference is then taken from the perineum above the trochanter. The residual limb is marked in two inch increments on the lateral side beginning at the level of the perineum. Short residual limbs should be marked in one inch increments.

It should be noted that these marks begin at the perineal level, not at the ischial tuberosity which is lower than the perineum. Failure to use this length measurement will result in a socket of insufficient length and will cause a space between the exit point of the ramus and the medial wall of the socket.

At each mark, a circumferential measurement is taken with slight tension of about ⅛ inch compression on the tissue. In the event a Silesian belt may be used, the distance between the trochanter and the anterior midline is determined. The distance from the adductor longus muscle to the greater trochanter is measured. Also, the distance from the ischial tuberosity to the adductor longus muscle is measured.

Measurements are taken on the patient's unaffected limb. First, the distance between the floor and the perineum is measured. The knee center is determined, and the distance from the floor to this point is measured. To this is added about ⅜ inch for the average child and 1 and ⅝ inch for the average adult. These distances serve as guidelines. The distance from the floor to the medial tibial plateau is measured.

The point at which the circumference of the ankle is smallest next is noted and measured. Then, the distance between this point and the floor is taken. The point at which the circumference of the calf is greatest is noted and measured. Then, the distance between this point and the floor is taken. The foot is measured, and the knee width is determined.

Having completed the physical assessment of the residual thigh, a negative model of the thigh is produced by forming a cast over it. The patient is provided with well-fitting casting shorts. The shorts should be closely conformed to the body, that is, formed into the coccyx and the symphysis pubis areas. However, care should be taken that the shorts are not too tight, as this will prevent gaining access to the ischial tuberosity and the ramus during casting.

The end of the shorts which covers the residual limb is tied off and the excess material is cut away. The greater trochanter and the femoral distal relief area are marked on the shorts to allow for identification on the plaster model.

The proximal area of the residual limb is wrapped with four-inch elasticated plaster bandages. The plaster then is wrapped as high as possible, ensuring that the ramus, the ischial tuberosity and ischio-rectal fossa all are contained in the plaster.

The various muscle groups are then palpated, and the contours of the leg are identified and formed in the plaster. Although this phase of the fabrication procedure involves a plaster cast, reference will be made to the drawings which depict a permanent flexible socket as the contours are similar.

Figure 2A:
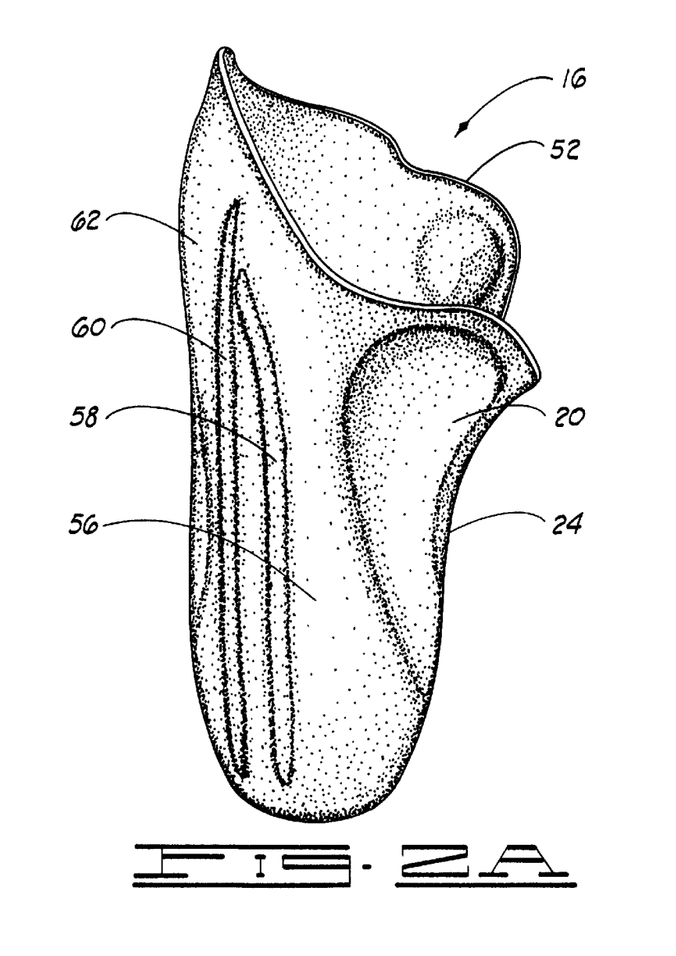
FIG. 2A is an anterior elevational view of a socket for a prosthesis in accordance with a first embodiment of the present invention.

Referring now to FIG. 2A, which shows an anterior view of the socket 16, the first contour to be identified and formed in the cast preferably is a depression in the groin area, part of which is the femoral triangle or Scarpa's Triangle. Scarpa's Triangle generally is defined proximally by the inguinal ligament, laterally by the sartorius muscle and medially by the adductor longus muscle. A contour in the form of an elongate anterior-medial triangular depression channel 20 is formed in the cast (and the socket) and extends over the femoral triangle. The channel 20 conforms to an area generally defined laterally by the sartorius muscle, medial-proximally by the lateral and inferior aspect of the adductor longus muscle, medial-distally by the anterior aspect of the gracilis muscle, and proximally by the inguinal ligament The channel 20 posts the adductor longus muscle. In addition, the sartorius muscle and the vastus medialis muscle have a channel in the socket against which they can exert pressure. Thus, when the muscle contracts, it presses against the sides of the channel, in effect, gripping the channel. This gives the patient increased support and control over the prosthesis. In addition, it allows the muscle to be exercised, thereby reducing atrophy. Other depressions, channels and inverse channels to be explained later produce like results.

Figure 2B:
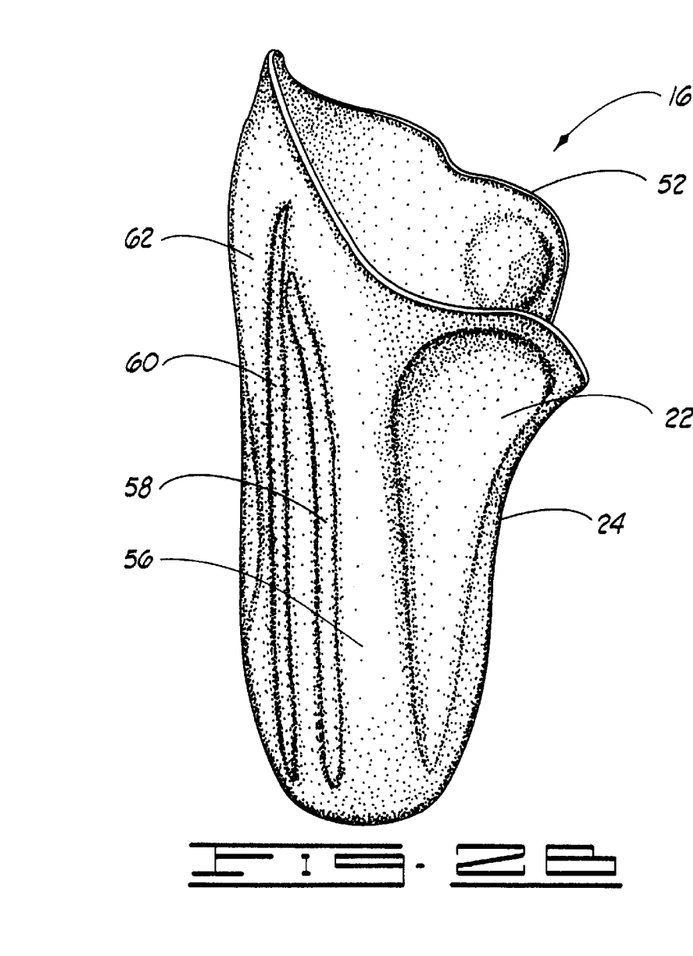
FIG. 2B is an anterior elevational view of a socket for a prosthesis in accordance with a second embodiment of the present invention.

If the adductor longus muscle in the residual has atrophied, the elongate anterior-medial depression channel 20 is modified as illustrated in FIG. 2B. The modified elongate anterior triangular depression channel 22 of FIG. 2B generally is bordered laterally by the proximal aspect of the sartorius muscle and the distal-medial aspect of the rectus femoris muscle, medially by the proximal-lateral aspect of the adductor longus muscle, and proximally by the inguinal ligament. The triangular depression 22 may extend distally to the lateral aspect of the vastus medialis muscle. The triangular depression 22 preferably extends across the belly of the sartorius muscle and to the distal area of the residual limb between the vastus medialis muscle and the rectus femoris muscle.

Immediately posterior to the elongate anterior-medial triangular depression channel 20 of FIG. 2A, or the elongate anterior triangular depression channel 22 of FIG. 2B, is an elongate vertical prominence on the medial aspect of the thigh formed by the adductor longus muscle and the gracilis muscle. A corresponding prominence, referred to herein as the medial longitudinal inverted channel 24, is formed in the cast.

Figure 3A:
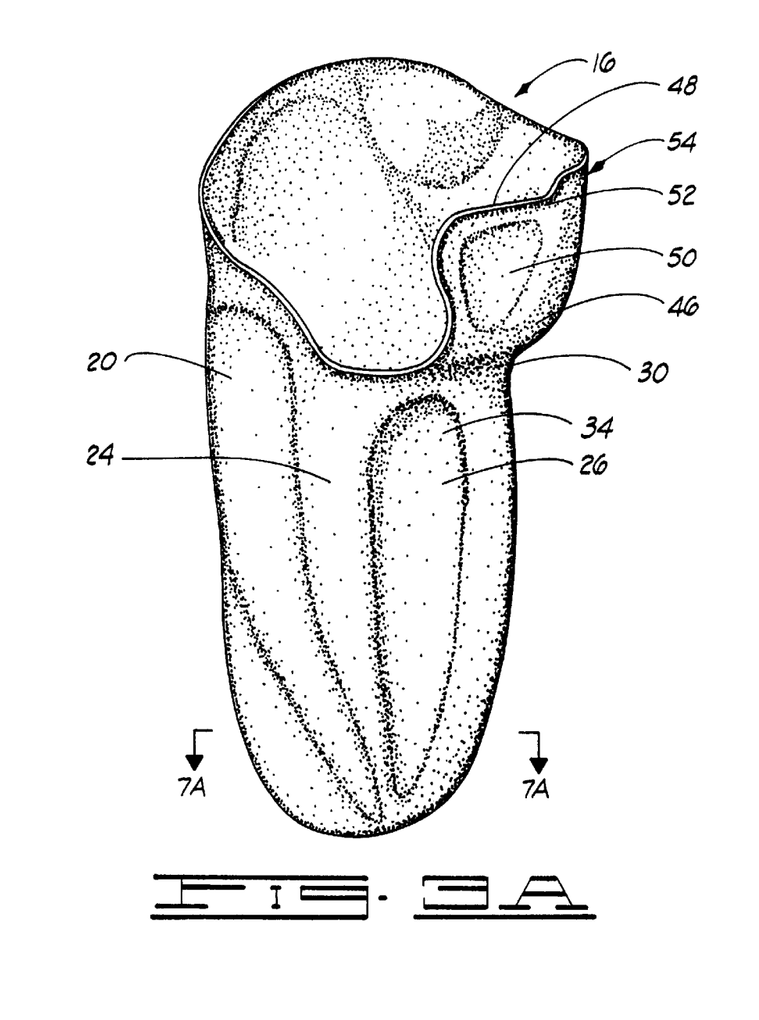
FIG. 3A is a medial elevational view of the socket shown in FIG. 2A.
Figure 3B:
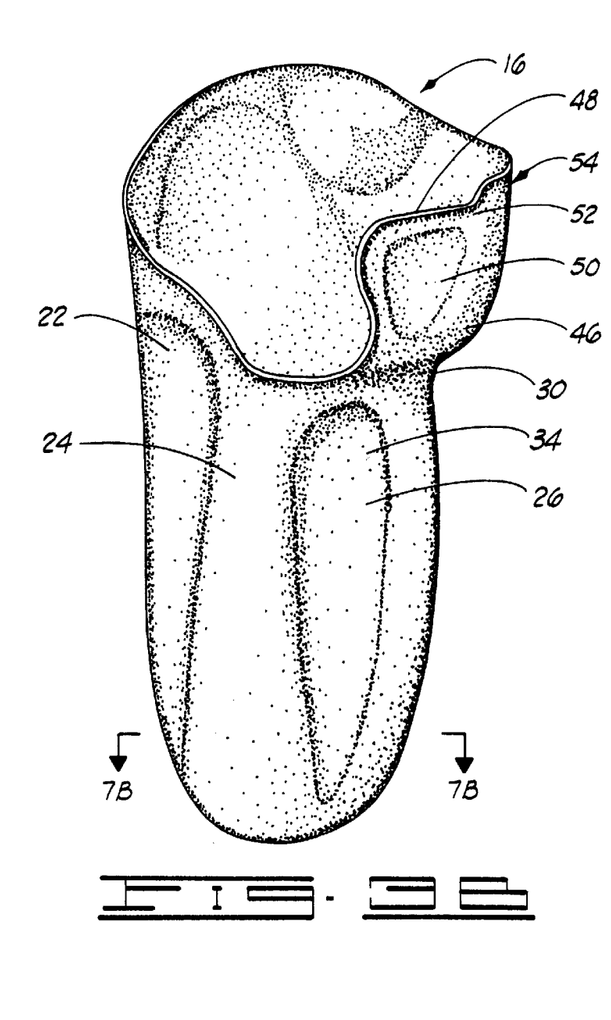
FIG. 3B is a medial elevational view of the socket shown in FIG. 2B.

Continuing to move medially, FIG. 3A and FIG. 3B show the medial view of the socket 16, with the elongate anterior-medial triangular depression channel 20 of FIG. 2A and the modified elongate anterior triangular depression channel 22 of FIG. 2B illustrated on the respective drawings. The medial aspect of the thigh has an inverted triangular contour generally defined proximally by the inferior border of the ramus of the ischium, anteriorly by the gracilis muscle, and posteriorly by a group of underlying muscles including the adductor magnus muscle, the semimembranosus muscle and the semitendinosus muscle. A corresponding depression is formed in the cast, which depression is referred to herein as the elongate medial triangular depression channel 26. Preferably, the channel 26 extends distally to conform substantially to the distal end of the muscles of the residual thigh. Note that the elongate medial triangular depression channel 26 is the same in both FIG. 3A and FIG. 3B. It is merely depicted in relation to the channels (the elongate anterior-medial triangular depression channel 20 and the modified elongate anterior triangular depression channel 22) depicted in FIG. 2A and FIG. 2B, respectively.

Figure 4:
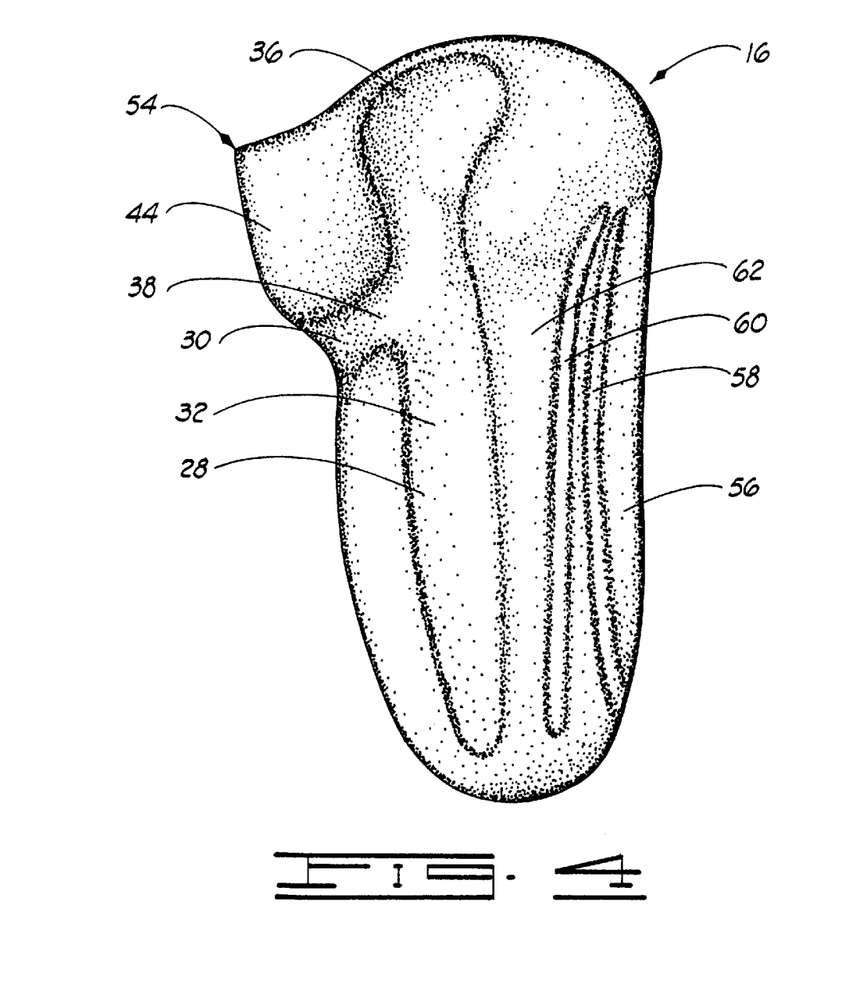
FIG. 4 is a lateral elevational view of the socket shown in FIG. 2B.

On the lateral side of the thigh there is an elongate vertical channel defined by the shape of the adjacent underlying muscles, such as the vastus lateralis muscle anteriorly and by the biceps femoris muscle (lateral head) posteriorly. Referring now to FIG. 4, a corresponding channel is formed in the cast, which channel is referred to herein as the elongate posterior-lateral longitudinal channel 28. Preferably, the elongate vertical channel 28 is shaped to conform substantially to the distal end of the muscles of the residual thigh.

Figure 5:
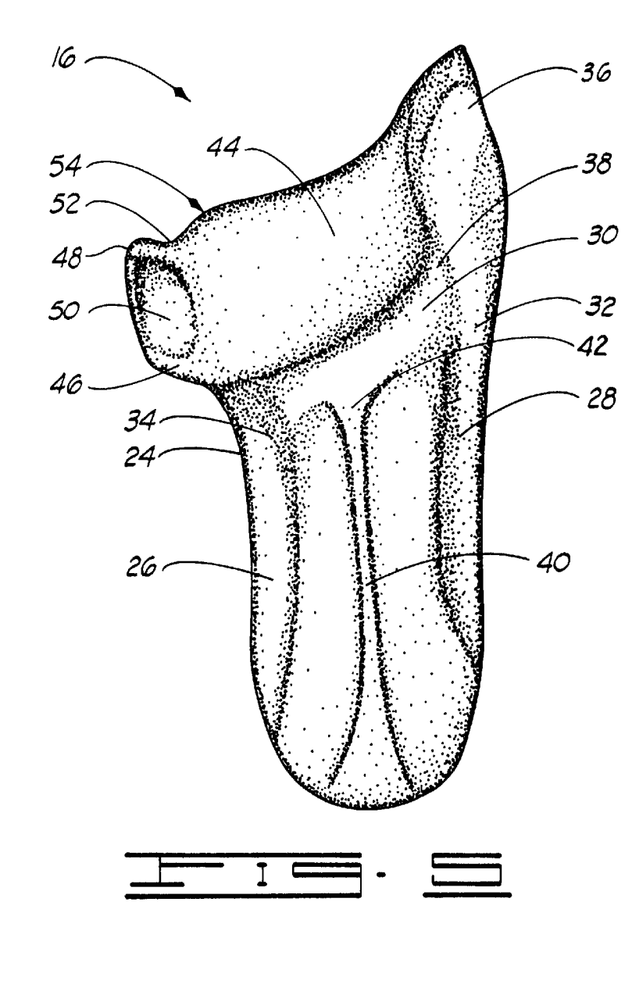
FIG. 5 is a posterior elevational view of the socket shown in FIG. 2B.

Continuing now to the posterior aspect of the thigh, attention is directed to FIG. 5. An elongate transverse depression is found in the posterior aspect of the residual thigh, which depression commonly is called the gluteal fold. The gluteal fold is defined proximally by the bulge or belly of the gluteus maximus muscle and distally by the area where the biceps femoris muscle (long head) and the semitendinosus muscle originate on the ischial tuberosity. A corresponding channel, referred to herein as the posterior transverse channel 30, is formed in the cast.

As shown in FIG. 5, the posterior transverse channel 30 in the socket 16 extends laterally across the back of the socket 16 to intersect the proximal end 32 of the elongate posterior-lateral longitudinal channel 28 (FIGS. 4 and 5) and medially to intersect the proximal-medial corner 34 of the elongate medial triangular depression channel 26 (FIGS. 3A, 3B and 5).

Still referring to FIG. 5, proximal to the elongate posterior-lateral longitudinal channel 28 there is formed a lateral rounded depression 36. This depression corresponds to the posterior trochanteric fossa which is seen in thin muscularly developed individuals and sometimes is referred to as "the wallet hollow." The distal or inferior aspect of the lateral rounded depression 36 is continuous with the proximal end 32 of the elongate posterior-lateral longitudinal channel 28 and the lateral end 38 of the posterior transverse channel 30.

With continued reference to FIG. 5, a posterior longitudinal triangular channel 40 is formed immediately inferior to the posterior transverse channel 30 between the elongate medial triangular depression channel 26 and the elongate posterior-lateral longitudinal channel 28. The posterior longitudinal triangular channel 40 conforms to a groove between the semitendinosus muscle and the biceps femoris muscle in the residual thigh. The channel 26 preferably extends substantially to the tendons at the distal end of the residual limb. In addition, in some patients, the channel 40 terminates superiorly in an inverted triangular shaped depression 42 where the posterior longitudinal triangle channel 40 intersects the posterior transverse channel 30.

As seen in FIGS. 4 and 5, immediately proximal or superior to the posterior transverse channel 30 there is formed in the cast a gluteal shelf 44 which corresponds to the belly or bulge of the gluteus maximus muscle. As illustrated more clearly in FIG. 5, continuous with the gluteal shelf 44 and curving around medially (see also FIGS. 3A and 3B) is an ischio-ramal shelf 46 which is proximal to and protrudes over the elongate medial triangular depression channel 26. The ischio-ramal shelf 46 is shaped to contain the inferior border of the ramus and the ischial tuberosity.

Referring to FIGS. 3A, 3B and 5, a vertical wall 48 of the ischio-ramal shelf 46 in the cast defines a medial rounded depression 50. This depression in the socket 16 corresponds to the underlying obturator foramen.

Above and surrounding the medial rounded depression 50, is a medial-proximal compartment 52 (see also FIGS. 2A and 2B). The medial-proximal compartment 52 is adapted to receive the ischial tuberosity and ramus bone, along with the fatty tissue in the ischio-rectal fossa.

Referring again to FIG. 5, it can be seen that the gluteal shelf 44, the ischio-ramal shelf 46 and, to some extent, the lateral aspect of the socket 16 which defines the lateral rounded depression 36 tog ether create a gluteal containent compartment 54 (see also FIGS. 3A, 3B and 4). The gluteal containment compartment 54 is adapted to receive and support the ischio-rectal fossa, parts of the gluteus maximus and gluteus medius muscles and the associated bony and muscular formations of the buttock over the residual thigh.

Returning now to FIGS. 2A, 2B and 4, there is a large prominence on the anterior aspect of the residual thigh formed by the body of the rectus femoris muscle and the sartorius muscle. Over this muscular prominence there is formed in the cast a relatively large anterior longitudinal inverted channel 56.

A mid-lateral-posterior longitudinal channel 58 is shaped in the cast to conform to an elongate channel on the lateral thigh. The mid-lateral-posterior longitudinal channel 58 conforms substantially to an area generally defined posteriorly by the iliotibial band, anteriorly by the vastus lateralis, and proximally by the proximal aspect of the tensor-faciae latae and the proximal-lateral aspect of the rectus femoris. Preferably, the channel 58 is shaped to extend to the distal end of the socket substantially conforming to the muscles at the distal end of the residual thigh.

Moving laterally on the residual thigh toward the anterior, a contour is formed between the rectus femoris muscle and the vastus lateralis muscle. A corresponding channel is formed in the cast for a lateral-anterior longitudinal channel 60.

Finally, there is another large elongate prominence on the lateral aspect of the patient's residual thigh formed by the underlying femoral bone and ilio-tibial tract. Accordingly, there is formed in the cast a corresponding lateral longitudinal inverted channel 62 for containing this prominence. Now it will be seen that the mid-lateral-posterior longitudinal channel 58, the lateral-anterior longitudinal channel 60 and the elongate posterior-lateral longitudinal channel 28 (see FIG. 4) are shaped within the area defined by the lateral longitudinal inverted prominence 62.

Having formed the above-described channels, depressions and inverse channels in the plaster, the plaster is palpated to establish that the channels, depressions and inverse channels contain or engage the proper underlying anatomic features. The distal end of the residual limb is pushed into adduction using the prosthetist's knee, and the cast then is allowed to set.

Once the cast, which is applied only to the upper portion of the residual limb is firm or set, the remainder of the residual limb is wrapped beginning at the distal end. Applying the plaster wrap in an upward direction, edema present in the limb is pushed upward toward the body rather than being trapped in the end of the limb.

Alignment of the cast is verified. With the patient standing as straight as possible, a plumb line is used to establish the alignment of the lateral side from the transverse axis of the hip joint. The trochanter can be posterior or anterior to the transverse axis.

By palpating through Scarpa's Triangle in the residual thigh, the anterior border of the acetabulum is located. A distance of ⅞ inch from the anterior border toward the posterior is measured to determine the approximate transverse axis of the hip joint. The gravity line bisects this point. A line is drawn from this point to the distal area of the cast in the desired amount of flexion.

The anterior alignment line next is determined. For this measurement, the cast should be adducted as far as possible. That is, the cast should be held as close to the unaffected limb as possible. The anterior alignment line should extend through the center of the cast proximally and through the distal femur.

The cast now may be removed. Immediately following removal of the cast, while the cast still is somewhat flexible, the medial-lateral dimension of the cast is measured and compared to the desired medial-lateral measurement. The width is adjusted, if necessary, to be within the preferred range. Again, while the negative cast still is flexible, the above-described contours of the cast are accentuated.

When the cast which forms the negative model is fully set, a positive plaster model may be made from the cast. The plaster model then is used to form the final socket. To form the positive model, the cast is secured in a wall fixture and filled with plaster. After the plaster has set, the cast is placed in a vice. By cutting the cast along the lateral wall, the plaster model may be removed. The plaster model then is measured, and these measurements are compared with the pre-casting measurements that were taken of the residual limb.

The angles of the model are noted. When viewed from the distal end of the model, the planes of the anterior, posterior and medial walls form an irregular triangle. Once the angle of the medial wall (from a horizontal plane) is established, this aspect of the cast may be modified by using a flat surform file and flattening the medial wall approximately one inch below the ischio-ramal shelf 46 (FIGS. 3A, 3B and 5) down to the distal end of the model. With a round surform file, the ramus is under cut following the exact angle of the ramus. (See pre-casting measurements for ramus angle.) In a similar manner, the vertical surface of the ischio-ramal shelf 46 is flattened parallel to the medial wall. The curvature of the ischio-ramal shelf 46 is refined with a half round surform file. All angles should be rechecked to ensure that they conform to the pre-casting measurements.

The line of progression and exit point for the ramus should be established. Working from the medial aspect of the positive model to the anterior area, the proximal anterior trimline of the model is squared to the line of progression. The angle of the ischio-ramal shelf 46, the medial wall, the anterior and the posterior walls should be rechecked. It should be noted that the angles are verified by viewing the model from the distal end, and, in order to produce the correct shape, the model should be checked from this position repeatedly during the modification procedure.

The curvature of the plaster model corresponding to the medial longitudinal inverted channel 24 (FIGS. 2A, 2B, 3A, 3B and 5) should be rounded using a half round surform file. The outer radius of the medial wall along the medial longitudinal inverted channel 24 should measure at least two inches. The radius should be checked with a pre-fabricated template, as the tendency is to make this too sharp and too tight a radius. A radius of less than two inches causes a corrugation effect in this area. This produces a rigid, uncomfortable socket.

The anterior wall of the plaster model next is flattened while maintaining the measured depths of the contours. The elongate anterior-medial triangular depression channel 20 of FIG. 2A (or the elongate anterior triangular depression channel 22 of FIG. 2B) is marked on the model, depending on the patient and whether the adductor longus muscle is hypotrophied, following the natural contours of the muscles. The depth of the depression, Class I, II, III, etc., should be verified against the pre-casting measurements of the residual limb.

The angle of the medial and lateral walls should be determined. The angle of the wall is the angle formed by the plane of the flattened surface of the wall and a vertical line, with the model supported horizontally. The lateral wall generally is about five degrees less in angulation than the medial wall. (See FIG. 6.) If the angle formed by the medial and lateral walls is too great, the posterior aspect of the socket will be too narrow. This results in the residual limb being pushed anteriorly in the socket 16, producing anterior pressure and medial-lateral pinching of the semimembranosus muscle, the semitendinosus muscle and the biceps femoris muscle.

Having established the angles for the medial and lateral walls, the modification of the lateral wall may be completed. First, the lateral wall is flattened with a surform file following the lateral surface of the femur. No material should be removed from the distal end of the model as this would decrease the volume of the distal relief area in the socket.

The length of the model is measured from the medial perineum area to the distal area. This measurement then is projected to the lateral wall, and the distance from the uppermost end of this measurement to the apex of the greater trochanter is taken. The ilio-femoral angle should be verified as correct, and the overall shape of the model should be examined for proper seating.

Posterior modification of the positive plaster model now may begin. Referring now to the drawings in general, first, the posterior transverse channel 30, which corresponds to the gluteal fold under the gluteal shelf 44 is located. This should touch or be adjacent or tangent to the ischial tuberosity and should intersect the elongate posterior-lateral longitudinal channel 28. The posterior transverse channel 30 is immediately under the gluteal shelf 44 and curves with the ischial tuberosity, providing more than merely a tangent force on this bony prominence. It is important to have a two inch radius to insure the patient's comfort.

The ischio-ramal shelf 46 is blended with a half round surform file. The shape of the model and measurements are checked again. The model should be marked in two-inch increments beginning at the perineum and extending to the distal area. Circumferential measurements are taken at each of the two-inch marks. It may be necessary to increase or decrease the size of the model to correspond to the pre-casting measurements of the residual limb. If the measurements are correct, the modification may proceed.

Next, the various contours of the model are carved. Depending on which was required, either the elongate anterior-medial triangular depression channel 20 or the elongate anterior triangular depression channel 22 is carved, preferably with a Scarpa's knife. Similarly, the elongate posterior-lateral longitudinal channel 28, the elongate medial triangular depression channel 26, the posterior longitudinal triangular channel 40, the mid-lateral posterior longitudinal channel 58, the lateral-anterior longitudinal channel 60 and the medial rounded depression 50 are carved. The contours should be shaped to have the depths—Class I, II, II, etc.—noted in the pre-casting measurements of the residual limb. Again it should be noted that no modification should be done to the distal relief area.

The model now should be finally evaluated. The shape of the model from the distal end is inspected. The angle of the anterior wall across the elongate anterior-medial triangular depression channel 20 (or the elongate anterior triangular depression channel 22) is examined. The degree of prominence of the anterior longitudinal inverted channel 56, which contains the rectus femoris muscle, the medial longitudinal inverted channel 24, which receives the gracilis muscle and the adductor longus muscle, and the anterior-posterior lateral longitudinal inverted channel 62 are examined to ensure these correspond to the desired depths.

The triangular shape of the model is examined. If the posterior angles are too severe, undue pressure on the anterior wall will be exerted on the limb while standing. In addition, the patient will experience problems during sitting, especially at the exit point of the ramus. Pinching of the semimembranosus muscle, the semitendinosus muscle and the biceps femoris while standing, walking or sitting may occur.

The line of progression of the model in relation to the medial trimline border of the socket is verified. The lateral wall of the model is examined for stabilization of the femur and to ensure adequate room in the femoral distal relief area.

The elongate anterior-medial triangular depression channel 20 (or the elongate anterior triangular depression channel 22) is remarked on the model using the procedure described previously. The depth of this contour should be reconfirmed.

The ischio-ramal shelf 46 and the medial rounded depression 50 should be examined. The depth of this depression should be about ¼ inch. The depths of the elongate medial triangular depression channel 26, the lateral rounded depression 36, the elongate posterior-lateral longitudinal channel 28 and the posterior transverse channel 30 all are examined, and all measurements of the model again are verified.

Having finally confirmed the correct measurements and contour configurations on the model, the diagnostic test socket may be fabricated. The test socket should have a wall thickness of 3/16 inch. The ischio-ramal shelf 46 should be at least 1 and ¼ inches wide.

When the test socket is completed, it is fitted carefully to the patent's residual limb. First, the limb is pulled in the socket. There should be no pressure on the ischial spine. In some overweight patients, the medial-proximal compartment 52 may hit and cause pressure on the coccyx. If this occurs, the medial-proximal compartment 52 must be lowered until there is no contact with either the coccyx or the ischial spine. This pressure area should be checked with the limb in extension and with the patient bearing weight on the socket.

Pressure on the ramus should not be excessive. Pressure on the ramus can be detected by placing one's index fingers end-to-end outside the ischio-ramal shelf 46. With the patient lifting his weight off of the socket, both index fingers are slipped inside the vertical wall 48 of the ischio-ramal shelf 46. Then, the ramus is palpated as the patient bears down on the socket. In this position, uneven anterior and posterior pressure can be palpated. If undue pressure is present, remove the socket and reapply it. Immediate adjustments should not be attempted.

While the socket is being reapplied and evaluated, it should be turned slightly away from the direction of the pressure. Using the same index-finger test, the presence of the pressure should be detected. If the pressure still is present, the socket should be relieved in this area. Once a comfortable shape has been obtained, the procedure should be repeated and the socket should be re-examined for pressure on the ischial spine during weight bearing. Again, in the case of an overweight patient, coccyx pressure should be located and relieved. When the pressure on the coccyx is removed, even weight distribution on the ramus and ischial tuberosity should be reconfirmed.

A portion of the weight on the socket 16 should be borne on the ischio-ramal shelf 46, while the remaining weight is evenly distributed through the socket 16. The ischio-ramal shelf 46 should not be straight. Rather, it should curve slightly to match the medial border of the ischium. Slight pressure should be carried on the soft fatty tissue over the ischial tuberosity.

It should be verified that the medial rounded depression 50 is correctly positioned over the obturator foramen fossa. The exit point of the ramus should be touching the socket 16 in this area without pressure during weight bearing. If this is not the case, correction should be made: the ischio-ramal shelf 46 at the exit point of the ramus may be too high; the angle of the medial-lateral wall may be too great in the posterior area; or, the ilio-femoral angle may be too tight.

If the patient has an adductor roll, this should be contained completely within the ischio-ramal shelf 46. The elongate anterior-medial triangular depression channel 20, or, alternatively, the elongate anterior triangular depression channel 22, should closely engage the femoral triangle. The adductor longus muscle and the gracilis muscle should be contained within the medial longitudinal inverted channel 24 of the socket 16. Similarly, the rectus femoris muscle and sartorius muscle should be contained within the anterior longitudinal inverted channel 56.

No tissue in the proximal area should protrude over the top of the socket 16. If tissue is protruding, correction is indicated: the anterior proximal wall may be too low or the medial-lateral angle may need increasing. Further, for maximum comfort, there should be relief for the anterior superior iliac spine when the patient sits.

The lateral wall of the socket should conform to the lateral thigh. If gaping is present, containment of the ischial tuberosity and the ramus should be verified. If the ramus and ischial tuberosity are well contained within the gluteal containment compartment 54, and if the fit is satisfactory, the proximal lateral wall is alginated.

It is particularly important to ensure that the ischial tuberosity and ramus are contained deeply within the gluteal containment compartment 54, that the ramus is well caught and not slipping out anteriorly, and that the ramus is sitting directly on the ischio-ramal shelf 46. As shown in FIG. 1, further support for the ischio-ramal shelf 46 can be provided by using a frame 14 with a medial flange 64 shaped to conform generally to the vertical wall 48 of the ischio-ramal shelf 46.

The greater trochanter should be contained within the proper prominence. The lateral rounded depression 36 of the socket 16 should closely engage the post-trochanteric fossa. However, it should be understood that excessive pressure in this area can produce excessive internal rotation.

The intersections formed in the socket 16 by the posterior transverse channel 30, the elongate posterior-lateral longitudinal channel 28 and the lateral rounded depression 36 in the socket 16 should be seated squarely in the corresponding anatomical depressions. The lateral femoral support should be flat and adequate to prevent abduction of the femur in the socket 16. The lateral distal relief area should be adequate to prevent distal pressure in the socket 16.

The gluteus maximus muscle should be contained securely in the gluteal shelf 44. Excessive tension should be relieved by stretching the circumference of the socket 16. Looseness in this area should be corrected by tightening. There should be no re-flare at the proximal trimline. There should be proper tension in the muscle belly, and all muscle groups should be properly seated.

Lateral compression of the soft tissue over the femur should be detected. For this purpose, the test socket is provided with ⅜-inch holes in this area (not shown). Pressure may be detected by using the eraser end of a pencil and probing on the tissue through the holes. Excessive pressure is present if tissue bulges excessively through the holes. This may be corrected by widening the medial-lateral or circumferential dimensions of the socket, as indicated.

Once a correct fit of the test socket 16 is achieved, the socket 16 is aligned using an alignment apparatus. The thigh should be adducted as much as possible. The transverse angle of the hip joint should be aligned with the knee and ankle. A plumb line should be used for this purpose. Having achieved static alignment, proper alignment throughout the gait cycle should be established, as well as an accurate overall fit and patient comfort.

Having completed alignment, the distal area of the socket next is alginated. As air will be trapped in the distal relief area of the socket, provision must be made for escape of this air. The pressure of the alginate should be measured. The alginate should feel similar to the soft tissue of the thenar eminence.

The test socket is removed and the algination is examined from inside the socket. Immediately upon removal, the patient's limb should be examined carefully. Any discolorations due to pressure points should be noted for correction before the permanent socket is fabricated.

The length of the test socket from the perineum to the floor should be recorded. Proper alignment lines should be clearly marked on the test socket. Now the test socket is ready for minor adjustments indicated during the above fitting procedure.

The permanent socket is fabricated and substituted for the test socket in the prosthesis. Only minor adjustments of the prosthesis should be necessary at this point.

It will be understood that in the permanent socket of the present invention there is a complex integration of various anatomical contours, as best appreciated from the plan view of the socket shown in FIG. 6. From the plan view perspective of FIG. 6, it can be seen that the socket 16 generally is triangular in cross-section defined by the following: a first plane defined generally by outer surfaces of the elongate anterior triangular depression channel 22 (or the elongate anterior-medial triangular depression channel 20), a second plane defined by the outer surfaces of the elongate medial triangular depression channel 26, and a third plane defined generally by the outer surfaces of the elongate posterior-lateral longitudinal channel 28. These planes are indicated by the broken lines in FIG. 6.

As more fully illustrated in FIG. 6, the internal configuration of the socket 16, if properly fitted to engage the corresponding anatomical structures of the patient's residual thigh, quite literally will grip the underlying structures to achieve a degree of fit, femoral stability and overall comfort not previously attained in above-the-knee sockets. As best illustrated in the cross-sections of the lower portion of the socket 16 (FIG. 7A and FIG. 7B), the contours of the elongate channels extend substantially to the distal end of the socket 16 to conform substantially to the muscles in distal portion of the residual thigh. These contours provide the patient with more control over the socket 16 by providing structures which the muscles of the lower residual limb can grip. Moreover, the improved fitted socket snugly contains the thigh and maintains it, throughout the gait cycle, in a proper anatomical position. This improved fit increases the comfort of the prosthesis and minimizes gait abnormalities which can occur with other artificial limbs. The increased support helps maintain the physical condition of the residual limb. The extended and new channels allow the muscles of the patient's residual thigh to flex and contract against and around the channels, thereby "exercising" the muscles and reducing effects of muscle atrophy.

Figure 7A:
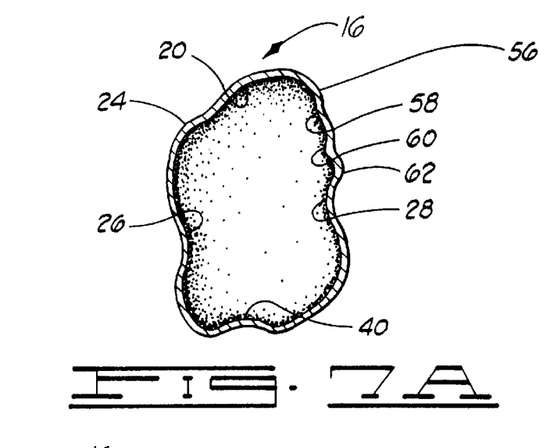
FIG. 7A is a cross-sectional view of the socket shown in FIG. 3A along line 7A—7A.
Figure 7B:
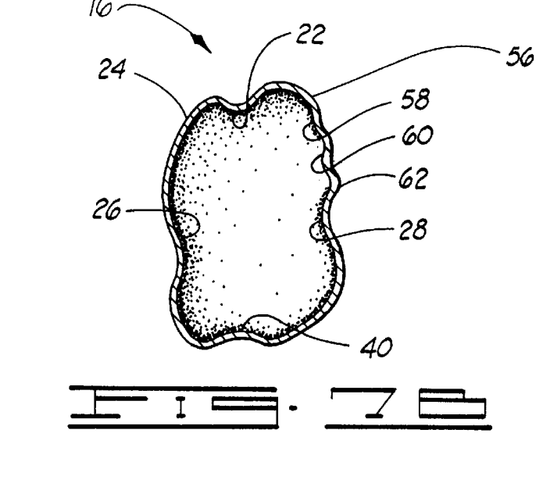
FIG. 7B is a cross-sectional view of the socket shown in FIG. 3B along line 7B—7B.
Figure 8:
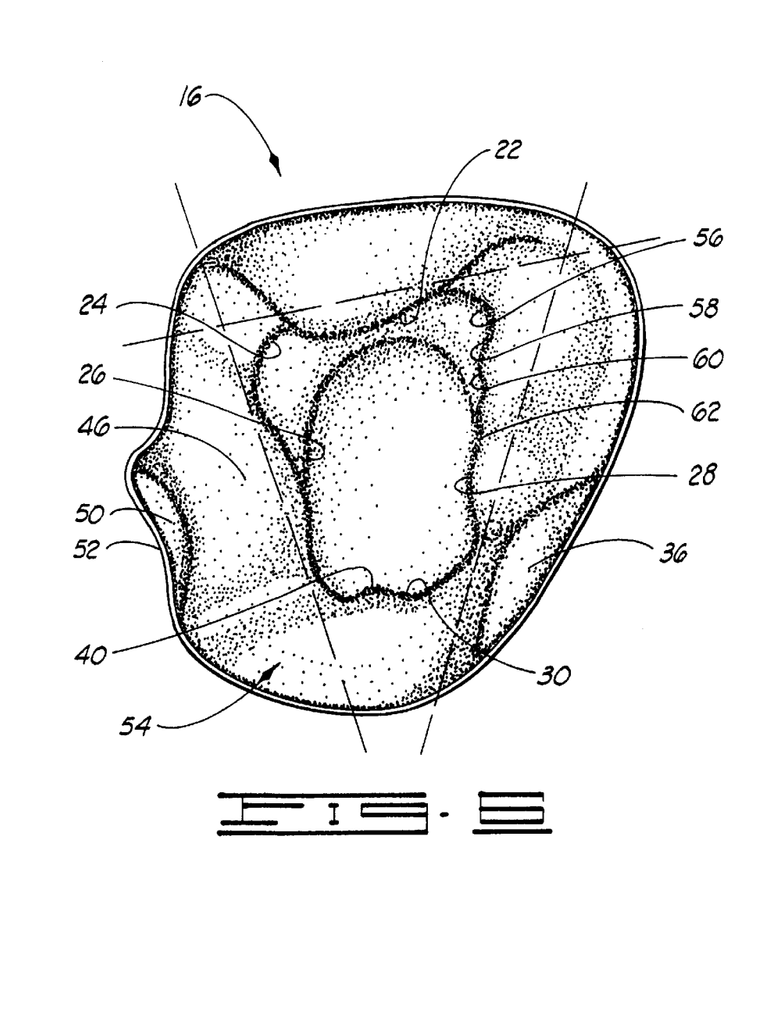

FIG. 7A illustrates a cross-section of FIG. 3A along line 7A—7A. FIG. 7B illustrates a cross-section of FIG. 3B along line 7B—7B. The two figures illustrate the difference in the contours for the elongate anterior-medial triangular depression channel 20 (FIG. 7A) and the elongate anterior triangular depression channel 22 (FIG. 7B) as seen in the lower portion of the socket 16. As illustrated, the contours are more medially rounded in FIG. 7A for the elongate anterior-medial triangular depression channel 20 and the medial longitudinal inverted channel 24. The medial slant occurs because the contours more closely follow the medial aspect of the sartorius muscle when the adductor longus muscle is not hypotrophied.

Sometimes, for reasons unrelated to the socket, fluctuations in the size or volume of the residual thigh may occur and alter the socket's fit, resulting in discomfort for the patient. With the present invention, the patient may make minor and temporary adjustments to the socket to accommodate occasional changes in the volume of the residual thigh. To this end, the prosthesis of the present invention may be equipped with the system of inflatable compartments 18, such as is illustrated in FIG. 1, and as described more fully in U.S. Pat. No. 5,246,464, the contents of which are hereby incorporated herein by reference.

Generally, each compartment is shaped to correspond to one of the previously described contours of the socket 16. The system 18 may include a compartment for any one or more of the contours of the socket 16. Preferably, the system 18 includes a plurality of compartments, as this provides the patient with a wider range of sizing options.

The system of inflatable compartments is secured to the socket in some suitable manner. For example, in the prosthesis 10 shown in FIG. 1, which includes a separately formed socket 16 and a rigid frame 14 inside the limb 12, the system 18 may be fixed between the frame 14 and socket 16. Positioned thusly, inflation of any of the compartments in the system 18 will press the adjacent contour of the socket 16 inwardly, the rigid frame 14 preventing expansion of the compartment outwardly. Likewise, deflation of any of the compartments will allow the socket 16 to return to its original shape, releasing the pressure on the associated area of the residual thigh. In this way, the internal contours and the fit of the socket 16 may be adjusted to accommodate volume fluctuations in the residual thigh.

It will be understood that the shape and dimensions of the anatomical contours described herein will vary somewhat among patients, and the contours depicted in the drawings are only illustrative. Further, while in most instances all the contours identified herein will be present to some extent, one or more of the contours may be omitted depending on the needs of the patient.

In most instances the contours in the socket will be slightly exaggerated as compared to the corresponding contour on the patient's thigh. For example, in less developed or overweight patients, the resting contour of the residual thigh may not distinctly exhibit one or more of the contours described herein. Yet, even in these patients, the exaggerated contouring of the socket of this invention permits the socket to "grip" the residual thigh by engaging the primary underlying muscles and bones rather than simply conforming to the outer contour of the patient's thigh at rest.

Changes may be made in the combination and arrangement of the various parts, elements, steps and procedures described herein without departing from the spirit and scope of the invention as defined in the following claims.

What is claimed is:

1. A prosthesis for the residual thigh of an above-the-knee amputee comprising:

a limb assembly; and a socket in the limb assembly, the socket characterized by an elongate anterior-medial triangular depression channel shaped to conform substantially to an elongate triangular depression generally defined laterally by the sartorius muscle, medial-proximally by the lateral and inferior aspect of the adductor longus muscle, medial-distally by the anterior aspect of the gracilis muscle, and proximally by the inguinal ligament.

2. The prosthesis of claim 1 further comprising:

an inflatable compartment corresponding to the elongate anterior-medial triangular depression channel;

wherein the inflatable compartment is operatively associated with the socket for adjustment of the contour of the socket to accommodate changes in the volume of the residual thigh.

3. A prosthesis for the residual thigh of an above-the-knee amputee comprising:

a limb assembly; and a socket in the limb assembly, the socket characterized by an elongate anterior triangular depression channel shaped to conform substantially to an elongate triangular depression generally defined laterally by the proximal aspect of the sartorius muscle and the distal-medial aspect of the rectus femoris muscle, medially by the proximal-lateral aspect of the adductor longus muscle, and proximally by the inguinal ligament, wherein the triangular depression distally extends to the lateral aspect of the vastus medialis muscle, and wherein the triangular depression extends across the sartorius muscle and between the vastus medialis muscle and the rectus femoris muscle.

4. The prosthesis of claim 3 further comprising:

an inflatable compartment corresponding to the elongate anterior triangular depression channel;

wherein the inflatable compartment is operatively associated with the socket for adjustment of the contour of the socket to accommodate changes in the volume of the residual thigh.

\* \* \* \* \*